United States Patent
Alocilja et al.

(10) Patent No.: US 8,936,946 B2
(45) Date of Patent: Jan. 20, 2015

(54) BIOLOGICALLY ENHANCED ELECTRICALLY-ACTIVE MAGNETIC NANOPARTICLES FOR CONCENTRATION, SEPARATION, AND DETECTION APPLICATIONS

(75) Inventors: Evangelyn C. Alocilja, East Lansing, MI (US); Sudeshna Pal, Okemos, MI (US); Emma B. Setterington, DeWitt, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 246 days.

(21) Appl. No.: 12/214,325

(22) Filed: Jun. 18, 2008

(65) Prior Publication Data
US 2009/0123939 A1    May 14, 2009

Related U.S. Application Data

(60) Provisional application No. 60/936,424, filed on Jun. 20, 2007.

(51) Int. Cl.
*G01N 33/543* (2006.01)
*G01N 27/74* (2006.01)

(52) U.S. Cl.
CPC .......... *G01N 33/5438* (2013.01); *G01N 27/745* (2013.01); *G01N 33/54333* (2013.01)
USPC .......................................... 436/526; 436/518

(58) Field of Classification Search
CPC ..................... C12Q 2563/155; C12Q 2563/00; G01N 33/54326; G01N 33/54353; G01N 33/54346; G01N 33/54333
USPC .................................................. 436/526, 518
See application file for complete search history.

(56) References Cited

U.S. PATENT DOCUMENTS

| | | |
|---|---|---|
| 4,486,530 A | 12/1984 | David et al. |
| 4,786,589 A | 11/1988 | Rounds et al. |
| 4,939,096 A | 7/1990 | Tonelli |
| 4,965,187 A | 10/1990 | Tonelli |
| 5,166,078 A | 11/1992 | McMahon et al. |
| 5,169,789 A | 12/1992 | Bernstein et al. |
| 5,177,014 A | 1/1993 | O'Connor et al. |
| 5,219,725 A | 6/1993 | O'Connor et al. |
| 5,256,372 A | 10/1993 | Brooks et al. |

(Continued)

OTHER PUBLICATIONS

Sharma et al. "Composition dependent magnetic properties of iron oxide-polyaniline nanoclusters". Journal of Applied Physics 97, 014311 (2005).*

(Continued)

*Primary Examiner* — Bao Thuy L Nguyen
*Assistant Examiner* — Pensee Do
(74) *Attorney, Agent, or Firm* — Marshall, Gerstein & Borun LLP (57) ABSTRACT

The disclosure generally relates to a particulate composition formed from a conductive polymer (e.g., conductive polyanilines, polypyrroles, polythiophenes) bound to magnetic nanoparticles (e.g., Fe(II)- and/or Fe(III)-based magnetic metal oxides). The particulate composition can be formed into a biologically enhanced, electrically active magnetic (BEAM) nanoparticle composition by further including a binding pair member (e.g., an antibody) bound to the conductive polymer of the particulate composition. Methods and kits employing the particulate composition and the BEAM nanoparticle composition also are disclosed.

19 Claims, 5 Drawing Sheets

(56) References Cited

U.S. PATENT DOCUMENTS

| | | | |
|---|---|---|---|
| 5,312,762 | A | 5/1994 | Guiseppi-Elie |
| 5,356,785 | A | 10/1994 | McMahon et al. |
| 5,491,097 | A | 2/1996 | Ribi et al. |
| 5,518,892 | A | 5/1996 | Naqui et al. |
| 5,536,644 | A * | 7/1996 | Ullman et al. ............... 435/7.25 |
| 5,559,041 | A | 9/1996 | Kang et al. |
| 5,620,845 | A | 4/1997 | Gould et al. |
| 5,620,895 | A | 4/1997 | Naqui et al. |
| 5,627,026 | A | 5/1997 | O'Connor et al. |
| 5,656,448 | A | 8/1997 | Kang et al. |
| 5,670,031 | A | 9/1997 | Hintsche et al. |
| 5,695,928 | A | 12/1997 | Stewart et al. |
| 5,700,655 | A | 12/1997 | Croteau et al. |
| 5,726,010 | A | 3/1998 | Clark |
| 5,726,013 | A | 3/1998 | Clark |
| 5,728,587 | A | 3/1998 | Kang et al. |
| 5,750,333 | A | 5/1998 | Clark |
| 5,753,456 | A | 5/1998 | Naqui et al. |
| 5,976,896 | A | 11/1999 | Kumar et al. |
| 5,985,594 | A | 11/1999 | Croteau et al. |
| 6,136,554 | A * | 10/2000 | Bochner ........................ 435/34 |
| 6,315,926 | B1 | 11/2001 | Jansen |
| 6,331,356 | B1 | 12/2001 | Angelopoulos |
| 6,333,145 | B1 | 12/2001 | Cloots |
| 6,333,425 | B1 | 12/2001 | Michot |
| 6,478,938 | B1 | 11/2002 | Paek et al. |
| 6,548,264 | B1 * | 4/2003 | Tan et al. ..................... 435/7.21 |
| 7,541,004 | B2 | 6/2009 | Niksa et al. |
| 2003/0153094 | A1 | 8/2003 | Alocilja et al. |
| 2003/0170613 | A1 * | 9/2003 | Straus ............................... 435/5 |
| 2003/0178309 | A1 | 9/2003 | Huang et al. |
| 2005/0009002 | A1 * | 1/2005 | Chen et al. ........................ 435/4 |
| 2007/0020700 | A1 | 1/2007 | Carpenter et al. |
| 2008/0305963 | A1 | 12/2008 | Alocilja et al. |

OTHER PUBLICATIONS

J.-H. Kim, et al., Conductimetric Membrane Strip Immunosensor with Polyaniline-Bound Gold Colloids as Signal Generator. Bio. and Bioelectronics (Feb. 2000); 14(12): 907-915.

Zhu N., et al., (2006), Electrochemically Fabricated Polyaniline Nanowire-Modified Electrode for Voltammetric Detection of DNA Hybridization. Electro. Acta, 51, 3758-3762.

Muhammad-Tahir et al, (2003b), Fabrication of a disposable biosensor for *Escherechia coli* 0157:H7 Detection. IEEE Sensor Journal, 3(4), 345-351.

Pal, S., et al., Biosensors & Bioelectronic, 2007, 22, 2329-2336.

N.L. Rosi, et al., Nanostructures in Biodiagnostics. Chem. Reviews (Apr. 2005); 105(4): 1547-1562.

S.-J. Park, et al., Array-Based Electrical Detection of DNA with Nanoparticle probes. Sci. (Feb. 2002); 295 (5559): 1503-1506.

S. Dubus, et al, PCR-Free DNA Detection Using a Magnetic Bead-Supported Polymeric Transducer and Microelectromagnetic Traps. Anal. Chem. (Jul. 1, 2006); 78(13):4457-4464.

G. Farace, et al., Reagentless Biosensing Using Electrochemical Impedance Spectroscopy. Bioelectrochemistry (Jan. 2002): 55(1-2): 1-3.

K.Y. Chumbimuni-Torres, et al., Solid Contact Potentiometric Sensors for Trace Level Measurements. Anal. Chem. (Feb. 15, 2006); 78(4): 1318-1322.

P.Poddar, et al., Magnetic Properties of Conducting Polymer Doped with Manganese—Zinc Ferrite Nanoparticles. Nanotechnology (Oct. 2004); 15(10): S570-S574.

W. Luo, et al. s-Electron Ferromagnetism in gold and Silver Nanoclusters. Nano Letters (Oct. 2007); 7(1): 3134-3137.

Stejskal J., "Polyaniline. Preparation of a Conducting Polymer," Pure Appln. Chem., vol. 74, No. 5, pp. 857-867 (2002).

* cited by examiner

BIOLOGICALLY ENHANCED ELECTRICALLY-ACTIVE MAGNETIC NANOPARTICLES FOR CONCENTRATION, SEPARATION, AND DETECTION APPLICATIONS

CROSS REFERENCE TO RELATED APPLICATIONS

Priority to U.S. Provisional Application Ser. No. 60/936,424, filed Jun. 20, 2007, which is incorporated herein by reference in its entirety, is claimed.

Related application to Alocilja et al. entitled "Electrically-Active Ferromagnetic Particle Conductimetric Biosensor Test Kit" which was filed on even date and also claimed priority to U.S. Provisional Application Ser. No. 60/936,424 ("the copending Alocilja application"), is also incorporated herein by reference in its entirety.

BACKGROUND OF THE DISCLOSURE

1. Field of the Disclosure

The disclosure generally relates to a particulate composition formed from a conductive polymer (e.g., conductive polyanilines, polypyrroles, polythiophenes) bound to magnetic nanoparticles (e.g., Fe(II)- and/or Fe(III)-based ferromagnetic magnetic metal oxides). The particulate composition can be formed into a biologically enhanced, electrically active magnetic (BEAM) nanoparticle composition by further including a binding pair member (e.g., an antibody) bound to the conductive polymer of the particulate composition.

2. Brief Description of Related Technology

Polymers, once used for insulating purposes, have gained prominence for electrical conductivity, among other novel traits such as magnetism and biodegradability. The appellation "synthetic metals" has been duly given to these polymers that exemplify the conductive/magnetic properties of the metallic inorganics (e.g., iron), as well as the flexibility and lightness of plastics. Conducting polymers can be utilized in diverse areas ranging from corrosion protection to microwave shielding. Analytical chemistry and chemical/biological sensors are significant areas of applications as well. The conductive properties of the synthetic metals arise from the $\pi$-electron backbone and the single/double bonds of the $\pi$-conjugated system alternating down the polymer chain. Some conducting polymeric structures include polyaniline (PANi), polypyrrole, polyacetylene, and polyphenylene. Polyaniline, in particular, has been studied thoroughly because of its stability in fluid form, conductive properties, and strong bio-molecular interactions. Conductive polymers can be used in a biosensor, an analytical device capable of pathogen detection in which the conductive polymers act as electrochemical transducers to transform biological signals to electric signals that can be detected and quantified.

Detection technologies employing magnetic particles or microbeads have been used. These particles bind with the target analyte in a sample being tested, for example using a binding pair member specific to the target analyte, and are then typically isolated or separated out of solution magnetically. Once isolation has occurred, other testing may be conducted to detect the presence of analyte-bound particles. For example, various types of immunoassays based upon detecting a signal from a capture reagent are described in U.S. Pat. No. 5,620,845 to Gould et al.; U.S. Pat. No. 4,486,530 to David et al.; U.S. Pat. No. 5,559,041 to Kang et al.; U.S. Pat. No. 5,656,448 to Kang et al.; U.S. Pat. No. 5,728,587 to Kang et al.; U.S. Pat. No. 5,695,928 to Stewart et al.; U.S. Pat. No. 5,169,789 to Bernstein et al.; U.S. Pat. Nos. 5,177,014, 5,219,725, and 5,627,026 to O'Conner et al.; U.S. Pat. No. 5,976,896 to Kumar et al.; U.S. Pat. Nos. 4,939,096 and 4,965,187 to Tonelli; U.S. Pat. No. 5,256,372 to Brooks et al.; U.S. Pat. Nos. 5,166,078 and 5,356,785 to McMahon et al.; U.S. Pat. Nos. 5,726,010, 5,726,013, and 5,750,333 to Clark; U.S. Pat. Nos. 5,518,892, 5,753,456, and 5,620,895 to Naqui et al.; U.S. Pat. Nos. 5,700,655 and 5,985,594 to Croteau et al.; and U.S. Pat. No. 4,786,589 to Rounds et al. The aforementioned U.S. patents are hereby incorporated herein by reference herein in their entireties.

Statistics has shown that pathogens result in an estimated 14 million illnesses, 60,000 hospitalizations, 1,800 deaths, and cost approximately $2.9-$6.7 billion in the United States each year due to food-borne diseases (e.g., resulting from infection by *Escherichia coli* O157:H7). Furthermore, possible bioterror threats has presented urgent needs of biosensors for surveillance of foods to prevent the contamination of food supplies. Of these numerous food-borne pathogens, *Bacillus cereus* has garnered notice as bacteria that can cause two types of food poisoning: a diarrheal type, and an emetic type. The former leads to diarrhea while the latter results in vomiting. The ubiquitous nature of the *Bacillus cereus* pathogen is demonstrated by its status as a common soil saprophyte and association with foods, primarily plants, but also meats, eggs, and dairy products. It was implicated in a third of all cases of food poisoning in Norway (1988-1993), 47% in Iceland (1985-1992), and 22% in Finland (1992). Furthermore, recent research has concluded that *Bacillus anthracis* and *Bacillus cereus* are of the same species. *B. anthracis* is responsible for the lethal disease anthrax, an agent in biological terrorism/warfare. Thus, detection and defense against *B. cereus* may accurately model and lead to heightened security with respect to *B. anthracis*.

Identification of pathogens by conventional methods, however, necessitates manual work and anywhere from 24 to 48 hours of incubation time. Thus, there exists a need for improved methods and compositions useful for the rapid, accurate, and selective detection of various pathogens.

SUMMARY

A particulate composition formed from a conductive polymer (e.g., conductive polyanilines, polypyrroles, polythiophenes) bound to magnetic nanoparticles (e.g., Fe(II)- and/or Fe(III)-based magnetic metal oxides) is disclosed. The particulate composition can be formed into a biologically enhanced, electrically active magnetic (BEAM) nanoparticle composition by further including a binding pair member (e.g., an antibody) bound to the conductive polymer of the particulate composition. Methods and kits employing the particulate composition and the BEAM nanoparticle composition also are disclosed.

In one embodiment, a particulate composition comprises a conductive polymer bound to magnetic nanoparticles. Preferably, the conductive polymer is selected from the group consisting of polyanilines (more preferred), polyparaphenylenes, polyparaphenylene vinylenes, polythiophenes, polypyrroles, polyfurans, polyselenophenes, polyisothianapthenes, polyphenylene sulfides, polyacetylenes, polypyridyl vinylenes, conductive carbohydrates, conductive polysaccharides, derivatives thereof, combinations thereof, blends thereof with other polymers, and copolymers of the monomers thereof. Preferably, the magnetic nanoparticles comprise ferromagnetic nanoparticles (e.g., $\gamma\text{-}Fe_2O_3$ (maghemite)).

In a further embodiment, a particulate composition comprises (a) magnetic nanoparticles comprising at least one of Fe(II) and Fe(III) (preferably $\gamma$-Fe$_2$O$_3$); and, (b) a conductive polymer bound to the magnetic nanoparticles, the conductive polymer being selected from the group consisting of polyanilines, polypyrroles, polythiophenes, derivatives thereof, combinations thereof, blends thereof with other polymers, and copolymers of the monomers thereof. Preferably, the particulate composition comprises particles ranging in size from about 10 nm to about 200 nm. The weight ratio of conductive polymer to magnetic nanoparticles in the particulate composition preferably ranges from about 0.4 to about 0.8.

In yet another embodiment, a biologically enhanced, electrically active magnetic (BEAM) nanoparticle composition comprises (a) a particulate composition comprising a conductive polymer (e.g., polyanilines, polypyrroles, polythiophenes, derivatives thereof, combinations thereof, blends thereof with other polymers, and copolymers of the monomers thereof) bound to magnetic nanoparticles (e.g., at least one of Fe(II) and Fe(III)); and, (b) a binding pair member bound to the conductive polymer of the particulate composition. Preferably, the binding pair member is selected from the group consisting of antibodies (more preferred; for example an anti-*Escherichia coli* O157:H7 antibody, an anti-*Bacillus anthracis* antibody, or an anti-*Bacillus cereus* antibody), antibody fragments, antigens, biotin, avidin and derivatives thereof, hormones, hormone receptors, polynucleotides, aptamers, whole cells, and combinations thereof. In an embodiment, the BEAM nanoparticles further comprise (c) a label bound to the conductive polymer of the particulate composition, for example labels such as enzymes, chromogenic substrates, chromophores, radioisotopes, fluorescent molecules, chemiluminescent molecules, phosphorescent molecules, direct visual labels, and combinations thereof.

Also disclosed is a method of detecting the presence of a target analyte in a sample, the method comprising: (a) providing a BEAM nanoparticle composition comprising (i) a particulate composition comprising: a conductive polymer bound to magnetic nanoparticles, and (ii) a binding pair member bound to the conductive polymer of the particulate composition, wherein the binding pair member is complementary to the target analyte; (b) contacting the BEAM nanoparticle composition with the sample for a time sufficient to bind any target analyte in the sample to the binding pair member of the BEAM nanoparticles, thereby forming an analyte-nanoparticle complex; (c) applying a magnetic field to the sample and removing a portion of the sample that is substantially free from the analyte-nanoparticle complex, thereby forming a sample concentrate that contains substantially all of the analyte-nanoparticle complex; and, (d) determining the presence of the target analyte in the sample by detecting the analyte-nanoparticle complex in the sample concentrate. In an embodiment, step (d) further comprises: (d1) contacting the sample concentrate with a detection label for a time sufficient to bind the detection label to the analyte-nanoparticle complex, thereby forming a label-analyte-nanoparticle complex, wherein either (i) the detection label is complementary to the target analyte and the detection label binds to the target analyte bound to the analyte-nanoparticle complex or (ii) the detection label is complementary to the binding pair member and the detection label binds to a free binding pair member of the analyte-nanoparticle complex; (d2) removing free detection label that is not bound in the label-analyte-nanoparticle complex from the sample concentrate; and, (d3) detecting the detection label remaining in the sample concentrate that is bound in the label-analyte-nanoparticle complex. Preferably, the detection label comprises a label selected from the group consisting of enzymes, chromogenic substrates, chromophores, radioisotopes, fluorescent molecules, chemiluminescent molecules, phosphorescent molecules, direct visual labels, and combinations thereof.

A additional method of detecting the presence of a target analyte in a sample comprises: (a) providing a BEAM nanoparticle composition comprising (i) a particulate composition comprising: a conductive polymer bound to magnetic nanoparticles, and (ii) a binding pair member bound to the conductive polymer of the particulate composition, wherein the binding pair member is complementary to the target analyte; (b) contacting the BEAM nanoparticle composition with the sample for a time sufficient to bind any target analyte in the sample to the binding pair member of the BEAM nanoparticles, thereby forming an analyte-nanoparticle complex; (c) applying the sample to a capture region of a lateral flow assay device, the capture region comprising an immobilized binding pair member complementary to the target analyte, thereby retaining the analyte-nanoparticle complex in the capture region; and, (d) determining the presence of the target analyte in the sample by magnetically detecting the analyte-nanoparticle complex in the capture region.

Also disclosed is a kit comprising: (a) a container containing a composition comprising a conductive polymer bound to magnetic nanoparticles. In an embodiment, (i) the magnetic nanoparticles comprise at least one of Fe(II) and Fe(III), and (ii) the conductive polymer is selected from the group consisting of polyanilines, polypyrroles, polythiophenes, derivatives thereof, combinations thereof, blends thereof with other polymers, and copolymers of the monomers thereof. In another embodiment, the composition further comprises a binding pair member bound to the conductive polymer, the binding pair member being complementary to a target analyte. The kit can further comprise a detection label complementary to the target analyte or to the binding pair member and/or a lateral flow assay device comprising a capture region, the capture region comprising an immobilized binding pair member complementary to the target analyte.

Additional features of the disclosure may become apparent to those skilled in the art from a review of the following detailed description, taken in conjunction with the drawings, examples, and appended claims.

BRIEF DESCRIPTION OF THE DRAWINGS

For a more complete understanding of the disclosure, reference should be made to the following detailed description and accompanying drawings wherein.

While the disclosed compositions and methods are susceptible of embodiments in various forms, specific embodiments of the disclosure are illustrated in the drawings (and will hereafter be described) with the understanding that the disclosure is intended to be illustrative, and is not intended to limit the claims to the specific embodiments described and illustrated herein.

DETAILED DESCRIPTION

A particulate composition formed from a conductive polymer (e.g., conductive polyanilines) bound to magnetic nanoparticles (e.g., $\gamma\text{-Fe}_2\text{O}_3$) is disclosed. The particulate composition is alternatively referenced as an electrically-active magnetic ("EAM") nanoparticle composition. The particulate composition can be formed into a biologically enhanced, electrically active magnetic (BEAM) nanoparticle composition by further including a binding pair member (e.g., an antibody) bound to the conductive polymer of the particulate composition. Methods and kits employing the particulate composition and the BEAM nanoparticle composition also are disclosed. The disclosed compositions and methods are useful for the rapid, accurate, and selective detection of various pathogens (e.g., *E. coli* O157:H7, *B. anthracis*, and *B. cereus*) in assays exploiting the magnetic properties of the nanoparticle compositions (e.g., for analyte concentration) and using any of a variety of detection mechanisms (e.g., using an enzyme label for colorimetric detection).

The BEAM nanoparticle composition can perform a dual function of a magnetic concentrator and a transducer in biosensing applications. The magnetic properties of the BEAM nanoparticles serve the purpose of concentrating and separating specific target analytes from complex sample matrices, while the electrical properties of the BEAM nanoparticles can be exploited in various detection schemes, for example biosensing applications which can be based on a conductimetric or other suitable type of assay.

These EAM nanoparticle compositions can mimic the function of magnetic beads widely used as a separator for immunomagnetic separation in immunoassays, for hybridization with nucleic acid probes as capture reagents, as templates in PCR, and the like. In addition, the electrical and the magnetic properties of the nanoparticles or composites can also be exploited as molecular transducers in biosensors. Some of the major advantages of the compositions include:
1. Ability to perform the dual function of a magnetic concentrator as well as a biosensor transducer;
2. Ability to achieve faster assay kinetics since the compositions are in suspension and in close proximity to target analytes;
3. Increased surface area for the biological events to occur;
4. Minimized matrix interference due to the improved separation and washing steps;
5. Ability to magnetically manipulate the magnetic nanomaterials by using permanent magnets or electromagnets;
6. Ability to avoid complex pre-enrichment, purification or pre-treatment steps necessary in standard methods of detection;
7. Ability to design cheap, sensitive, highly specific and rapid detection devices for diverse targets by using different biological modifications; and
8. Ability to design different rapid detection devices using both electrical and magnetic properties of the BEAM nanoparticles.

Particulate Composition

The particulate compositions according to the disclosure generally include a conductive polymer bound to magnetic nanoparticles (e.g., a population of magnetic nanoparticles in which each nanoparticle generally has at least some conductive polymer bound thereto).

The conductive polymers according to the disclosure are not particularly limited and generally include any polymer that is electrically conductive. Preferably, the conductive polymer is fluid-mobile when bound to an analyte. Suitable examples of conductive polymers are polyanilines, polypyrrole, and polythiophenes, which are dispersible in water and are conductive because of the presence of an anion or cation in the polymer (e.g., resulting from acid-doping of the polymer or monomer). Other electrically conductive polymers include substituted and unsubstituted polyanilines, polyparaphenylenes, polyparaphenylene vinylenes, polythiophenes, polypyrroles, polyfurans, polyselenophenes, polyisothianapthenes, polyphenylene sulfides, polyacetylenes, polypyridyl vinylenes, biomaterials, biopolymers, conductive carbohydrates, conductive polysaccharides, combinations thereof and blends thereof with other polymers, copolymers of the monomers thereof. Conductive polyanilines are preferred. Illustrative are the conductive polymers described in U.S. Pat. Nos. 6,333,425, 6,333,145, 6,331,356 and 6,315,926. Preferably, the conductive polymers do not contain metals in their metallic form.

The conductive polymer provides a substrate for the subsequent attachment of a binding pair member bound thereto, which binding pair member is complementary to a target analyte and thereby forms a BEAM nanoparticle, as described below. The electrically conductive characteristics of the conductive polymer also can facilitate detection of an analyte bound to the BEAM nanoparticle, for example by measuring the electrical resistance or conductance through a plurality of BEAM nanoparticles immobilized in a capture region of conductimetric biosensor device. Additionally, an electrical current passing through plurality of BEAM nanoparticles can be used to induce a magnetic field, and properties such as magnetic permeability or mass magnetization can be detected and correlated to the presence of the target analyte in a sample.

The magnetic nanoparticles according to the disclosure are not particularly limited and generally include any nano-sized particles (e.g., about 1 nm to about 1000 nm) that can be magnetized with an external magnetic/electrical field. The magnetic nanoparticles more particularly include superparamagnetic particles, which particles can be easily magnetized with an external magnetic field (e.g., to facilitate separation or concentration of the particles from the bulk of a sample medium) and then redispersed immediately once the magnet is removed (e.g., in a new (concentrated) sample medium). Thus, the magnetic nanoparticles are generally separable from solution with a conventional magnet. Suitable magnetic nanoparticles are provided as magnetic fluids or ferrofluids, and mainly include nano-sized iron oxide particles ($Fe_3O_4$ (magnetite) or $\gamma\text{-Fe}_2\text{O}_3$ (maghemite)) suspended in a carrier liquid. Such magnetic nanoparticles can be prepared by superparamagnetic iron oxide by precipitation of ferric and ferrous salts in the presence of sodium hydroxide and subsequent washing with water. A suitable source of $\gamma\text{-Fe}_2\text{O}_3$ is Sigma-Aldrich (St. Louis, Mo.), which is available as a nanopowder having particles sized at <50 nm with a specific surface area ranging from about 50 $m^2/g$ to about 250 $m^2/g$. Preferably, the magnetic nanoparticles have a small size distribution (e.g., ranging from about 5 nm to about 25 nm) and uniform surface properties (e.g., about 50 $m^2/g$ to about 245 $m^2/g$).

More generally, the magnetic nanoparticles can include ferromagnetic nanoparticles (i.e., iron-containing particles providing electrical conduction or resistance). Suitable ferromagnetic nanoparticles include iron-containing magnetic metal oxides, for example those including iron either as Fe(II), Fe(III), or a mixture of Fe(II)/Fe(III). Non-limiting examples of such oxides include FeO, $\gamma$-$Fe_2O_3$ (maghemite), and $Fe_3O_4$ (magnetite). The magnetic nanoparticles can also be a mixed metal oxide of the type $M1_xM2_{3-x}O_4$, wherein M1 represents a divalent metal ion and M2 represents a trivalent metal ion. For example, the magnetic nanoparticles may be magnetic ferrites of the formula $M1Fe_2O_4$, wherein M1 represents a divalent ion selected from Mn, Co, Ni, Cu, Zn, or Ba, pure or in admixture with each other or in admixture with ferrous ions. Other metal oxides include aluminium oxide, chromium oxide, copper oxide, manganese oxide, lead oxide, tin oxide, titanium oxide, zinc oxide and zirconium oxide, and suitable metals include Fe, Cr, Ni or magnetic alloys.

The particulate composition is generally formed by the polymerization of a conductive polymer monomer (e.g., aniline, pyrrole) in a solution (e.g., aqueous) containing the magnetic nanoparticles. The polymerization solution generally includes an acid dopant (e.g., HCl) to impart electrical conductivity to the resulting polymer. The polymerization reaction is preferably initiated by the addition of an oxidant (e.g., ammonium persulfate). Upon completion of the polymerization reaction, the solution contains the particulate composition in which the resulting conductive polymer is bound to the magnetic nanoparticles. The magnetic nanoparticles and the monomer can be combined in any suitable weight ratio in the polymerization solution so that the resulting particulate composition has a desired balance of magnetic, electrical, and particle size properties. For example, the weight ratio of monomer:magnetic nanoparticles in the polymerization solution (or conductive polymer:magnetic nanoparticles in the resulting particulate composition) preferably ranges from about 0.01 to about 10, more preferably from about 0.1 to about 1 or about 0.4 to about 0.8, for example about 0.6. Similarly, the particulate composition preferably ranges in size from about 1 nm to about 500 nm, more preferably about 10 nm to about 200 nm or about 50 nm to about 100 nm.

Biologically Enhanced, Electrically Active Magnetic Nanoparticles

Preferably, the particulate composition in any of its above embodiments is extended to a biologically enhanced, electrically active magnetic (BEAM) nanoparticle composition by further including a binding pair member bound to the conductive polymer of the particulate composition. The binding pair member is selected to be complementary to a target analyte so that the BEAM nanoparticle composition can be used for the selective detection of the target analyte in a sample.

An analyte (or target analyte) generally includes a chemical or biological material, including living cells, in a sample which is to be detected using the BEAM nanoparticle composition. The analyte can include pathogens of interest (e.g., *E. coli* O157:H7, *B. anthracis*, and *B. cereus*). The analyte also may be an antigen, an antibody, a ligand (i.e., an organic compound for which a receptor naturally exists or can be prepared, for example one that is mono- or polyepitopic, antigenic, or haptenic), a single compound or plurality of compounds that share at least one common epitopic site, and a receptor (i.e., a compound capable of binding to an epitopic or determinant site of a ligand, for example thyroxine binding globulin, antibodies, enzymes, Fab fragments, lectins, nucleic acids, protein A, complement component Clq). In some embodiments, the term "analyte" also can include an analog of the analyte (i.e., a modified form of the analyte which can compete with the analyte for a receptor) that can also be detected using the BEAM nanoparticle composition.

A sample generally includes an aliquot of any matter containing, or suspected of containing, the target analyte. For example, samples can include biological samples, such as samples from taken from animals (e.g., saliva, whole blood, serum, plasma, urine, tears, and the like), cell cultures, plants; environmental samples (e.g., water); and industrial samples. Samples may be required to be prepared prior to analysis according to the disclosed methods. For example, samples may require extraction, dilution, filtration, centrifugation, and/or stabilization prior to analysis. For the purposes herein, "sample" can refer to either a raw sample as originally collected or a sample resulting from one or more preparation techniques applied to the raw sample.

The binding pair member (or specific binding partner) generally includes one of two different molecules, each having a region or area on its surface or in a cavity that specifically binds to (i.e., is complementary with) a particular spatial and polar organization of the other molecule. The binding pair members can be referenced as a ligand/receptor (or antiligand) pair. These binding pair members include members of an immunological pair such as antigen-antibody. Other specific binding pairs such as biotin-avidin (or derivatives thereof such as streptavidin or neutravidin), hormones-hormone receptors, IgG-protein A, polynucleotide pairs (e.g., DNA-DNA, DNA-RNA), DNA aptamers, and whole cells are not immunological pairs, but can be used as binding pair members within the context of the present disclosure.

Preferably, the binding pair members are specific to each other and are selected such that one binding pair member is the target analyte of interest and the other binding pair member is the constituent bound to the conductive polymer of the particulate composition. Binding specificity (or specific binding) refers to the substantial recognition of a first molecule for a second molecule (i.e., the first and second members of the binding pair), for example a polypeptide and a polyclonal or monoclonal antibody, an antibody fragment (e.g., a Fv, single chain Fv, Fab', or $F(ab')_2$ fragment) specific for the polypeptide, enzyme-substrate interactions, and polynucleotide hybridization interactions. Preferably, the binding pair members exhibit a substantial degree of binding specificity and do not exhibit a substantial amount of non-specific binding (i.e., non-covalent binding between molecules that is relatively independent of the specific structures of the molecules, for example resulting from factors including electrostatic and hydrophobic interactions between molecules).

Substantial binding specificity refers to an amount of specific binding or recognition between molecules in an assay mixture under particular assay conditions. Substantial binding specificity relates to the extent that the first and second members of the binding pair to bind only with each other and do not bind to other interfering molecules that may be present in the analytical sample. The specificity of the first and second binding pair members for each other as compared to potential interfering molecules should be sufficient to allow a meaningful assay to be conducted for the target analyte. The substantial binding specificity can be a function of a particular set of assay conditions, which includes the relative concentrations of the molecules, the time and temperature of an incubation, etc. For example, the reactivity of one binding pair member with an interfering molecule as compared to that with the second binding pair member is preferably less than about 25%, more preferably less than about 10% or about 5%.

A preferred binding pair member is an antibody (an immunoglobulin) that specifically binds to and is thereby defined as complementary with a particular spatial and polar organization of another molecule (e.g., an antigen). Antibodies generally include Y-shaped proteins on the surface of B cells that specifically bind to antigens such as bacteria, viruses, etc. The antibody can be monoclonal or polyclonal and can be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b, IgG3, IgM, etc. Fragments thereof may include Fab, Fv and F(ab')$_2$, and Fab'. In addition, aggregates, polymers, and conjugates of immunoglobulins or their fragments can be used where appropriate so long as binding affinity for a particular molecule is maintained. Preferred antibodies include an anti-*Escherichia coli* O157:H7 antibody, an anti-*Bacillus anthracis* antibody, and an anti-*Bacillus cereus* antibody.

The binding pair member that is specific to the target analyte can be bound to the conductive polymer of the particulate composition by any of a variety of methods known in the art appropriate for the particular binding pair member (e.g., antibody, DNA oligonucleotide). For example, antibodies can be bound to the conductive polymer of the particulate composition by incubating the antibodies in a buffer (e.g., a phosphate buffer at a pH of about 7.4 containing dimethylformamide and lithium chloride) suspension of the particulate composition. Similarly, oligonucleotides can be incubated in a buffer (e.g., an acetate buffer at a pH of about 5.2) suspension of the particulate composition that also includes an immunoconjugating agent (e.g., 1-ethyl-3-(3-dimethylaminopropyl) carbodiimide hydrochloride ("EDAC")). After a suitable incubation period (i.e., depending on the rate of binding between the binding pair member and the conductive polymer) the resulting BEAM nanoparticles can be blocked, washed, centrifuged, and then stored as a suspension (e.g., in aqueous LiCl for an antibody on a phosphate-buffered saline ("PBS") solution for an oligonucleotide).

Applications of BEAM Nanoparticles

Figure 1:
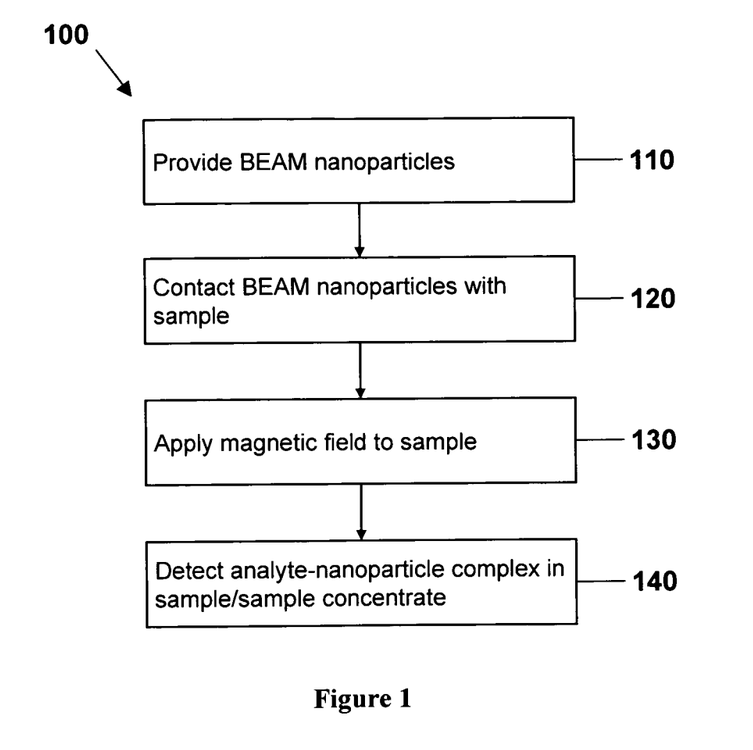
FIG. 1 illustrates a method of detecting the presence of a target analyte in a sample using a BEAM nanoparticle composition according to the disclosure.

The BEAM nanoparticles of any of the above embodiments can be used in an assay to detect the presence of a target analyte in a sample. A general method 100 to detect the target analyte is illustrated in FIG. 1 and has a first step 110 of providing BEAM nanoparticles having a particular binding pair member selected to be complementary to the target analyte. For example, in an assay to detect *Escherichia coli* O157:H7, the BEAM nanoparticles can include an anti-*Escherichia coli* O157:H7 antibody bound to the conductive polymer of the particulate composition. The BEAM nanoparticles can be provided in a variety of forms, for example a liquid suspension, a powder, or as part of an assay device (e.g., in an application region of a lateral flow assay device).

In a second step 120, the BEAM nanoparticle composition is contacted with the sample for a time sufficient to bind any target analyte in the sample to the binding pair member of the BEAM nanoparticles, thereby forming an analyte-nanoparticle complex. The sample and BEAM nanoparticles can be contacted in any convenient way, for example by combining the two components in a reaction vessel (e.g., adding the sample to a suspension of BEAM nanoparticles, adding the BEAM nanoparticles to a liquid sample, adding each component to a third vessel). Alternatively, when the BEAM nanoparticles are provided in the application region of a lateral flow assay device, the sample (in liquid form) can be added to the application region of the lateral flow assay device. The contact time required to obtain sufficient binding between the target analyte and the binding pair member generally depends on the kinetics of the particular analyte-binding pair member interaction. However, sufficient contact times are generally short, for example less than about 20 minutes, more preferably ranging from about 2 minutes to about 10 minutes of from about 2 minutes to about 6 minutes. Contact times can be regulated directly in a reaction vessel, while the specific construction of the lateral flow assay device (e.g., membrane size and/or material selection) can be used to regulate the contact times in such a device.

In some embodiments (e.g., when the sample and BEAM nanoparticles are combined in a reaction vessel), a magnetic field can be applied in a step 130 to the sample to concentrate the analyte-nanoparticle complex. Specifically, the applied magnetic field attracts the magnetic nanoparticle portion of the analyte-nanoparticle complex, causing individual particles of the analyte-nanoparticle complex to migrate to and concentrate in a region of the assay reaction vessel. Thus, after migration of the complex, a portion of the sample that is substantially free from the analyte-nanoparticle complex can be removed (e.g., by draining, skimming, pipetting, etc.), thereby forming a sample concentrate that contains substantially all of the analyte-nanoparticle complex. Preferably, at least about 80 wt. % to about 90 wt. % of the analyte-nanoparticle complex is recovered in the sample concentrate. Similarly, the concentration factor (i.e., the ratio of the concentration of the analyte-nanoparticle complex in the sample concentrate as compared to the original sample) is at least about 5, more preferably in the range of about 10 to about 50. If desired, the sample concentrate can then be removed from the assay reaction vessel (e.g., with or without an additional wash fluid) for subsequent analyte detection.

The sample (or sample concentrate) is then analyzed in a step 140 to detect the presence of the analyte-nanoparticle complex. A positive identification of the analyte-nanoparticle complex in the sample (concentrate) indicates the presence of the target analyte in the original sample. If a quantitative determination of the analyte-nanoparticle complex is made, any dilution and concentration factors can be used to determine the concentration of the target analyte in the original sample. The specific method of detection of the analyte-nanoparticle complex is not particularly limiting, and can include methods applicable to immunoassays in general or immunomagnetic assays in particular (e.g., agglomeration, spectrophotometric detection, colorimetric detection, radioactive detection, visual inspection).

For example, the sample can be applied to a capture region of a lateral flow assay device, where the capture region includes an immobilized binding pair member complementary to the target analyte (e.g., adsorbed onto a membrane). The sample can applied to the capture region in a variety of ways, such as by direct addition thereto or by capillary transport of the sample from an application region to the capture region. The immobilized binding pair member in the capture region retains the analyte-nanoparticle complex in the capture region. The presence of the target analyte in the sample can be determined by magnetically detecting the analyte-nanoparticle complex (i.e., the magnetic nanoparticle component thereof) in the capture region, inasmuch as BEAM nanoparticles that are not bound to analyte are transported by capillary action out of the capture region (e.g., into an absorption region of the device).

In an embodiment, the analyte-nanoparticle complex in the sample (concentrate) is detected by (1) contacting the sample with a detection label for a time sufficient to bind the detection label to the analyte-nanoparticle complex, thereby forming a label-analyte-nanoparticle complex, wherein either (i) the detection label is complementary to the target analyte and the detection label binds to the target analyte bound to the analyte-nanoparticle complex or (ii) the detection label is complementary to the binding pair member and the detection label binds to a free binding pair member of the analyte-nanoparticle complex, (2) removing any free detection label that is not bound in the label-analyte-nanoparticle complex from the sample (e.g., by washing), and (3) detecting the detection label remaining in the sample concentrate that is bound in the label-analyte-nanoparticle complex.

The detection label is generally part of a conjugate reagent that includes a label and an analyte-specific binding partner (in which case the detection label binds to the target analyte of the analyte-nanoparticle complex) or an analyte analog (in which case the detection label binds to free binding pair members of the analyte-nanoparticle complex). In an alternate embodiment, the detection label can be directly bound to the conductive polymer of the particulate composition. Such an embodiment can be useful, for example, when the labeled BEAM nanoparticles are used in a capture assay in which the labeled BEAM nanoparticles that are conjugated with the target analyte are immobilized in a capture region of a detection device such that the detection label can then facilitate detection of the target analyte in the capture region.

A label can include any molecule that is bound (via covalent or non-covalent means, alone or encapsulated) to another molecule or solid support and that is chosen for specific characteristics that allow detection of the labeled molecule. Generally, labels can include enzymes, chromogenic substrates, chromophores, radioisotopes, fluorescent molecules, chemiluminescent molecules, phosphorescent molecules, direct visual labels, and combinations thereof. Thus, the detection label can include labeled binding pair members that are complementary to the target analyte, for example including enzyme-, radioisotope-, and fluorescent ion-labeled antibodies. The utilization of a label produces a signal that may be detected by means such as detection of electromagnetic radiation, direct visualization, spectrophotometry, etc., which signal also can optionally be measured and/or quantitated. When the detection label binds to the target analyte (or to the conductive polymer directly in a capture assay), the measured signal is proportional to the amount of the analyte in the original sample; conversely, when the detection label includes an analyte analog that binds to the free binding pair members, the measured signal is inversely proportional to the amount of the analyte in the original sample.

The analyte-nanoparticle complex also can be detected in a conductimetric biosensor that uses the electrically conductive properties of the conductive polymer in the particulate composition to both detect and optionally quantify the analyte-nanoparticle complex. This particular method of detection is addressed in more detail in the copending Alocilja application.

Figure 2:
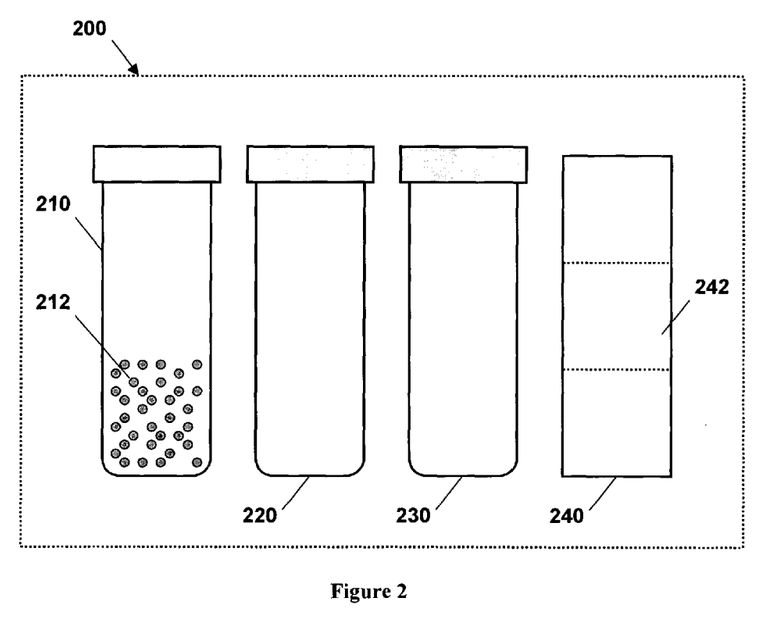
FIG. 2 illustrates a test kit containing compositions according to the disclosure.
Figure 3:
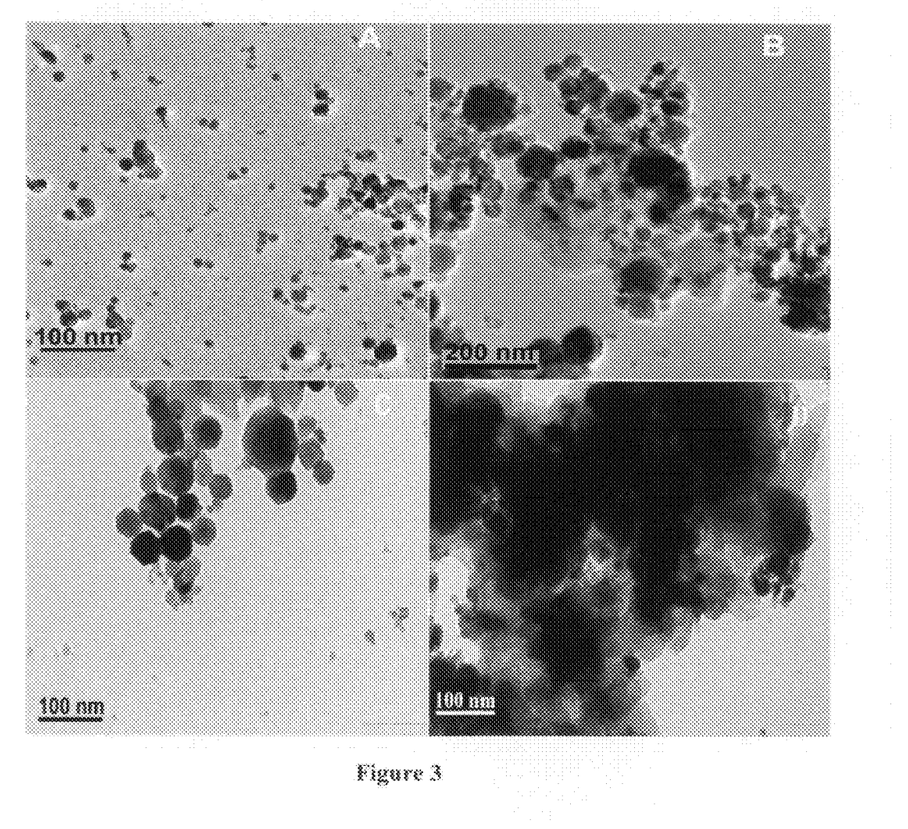
FIGS. 3A to 3D show TEM images of particulate compositions according to the disclosure including complexes of conductive polyaniline bound to $\gamma$-Fe$_2$O$_3$ at different weight ratios of $\gamma$-Fe$_2$O$_3$ to aniline (A: 1:0.1, B: 1:0.4, C: 1:0.6, and D: 1:0.8).

The disclosed compositions also can be provided in a variety of kits, for example as illustrated in FIG. 2. In one embodiment, a kit 200 includes a container 210 (e.g., glass vial, ampule) that contains any of the various compositions 212 according to the disclosure, for example as a powder or in a liquid suspension. More specifically, the composition 212 can be provided in a non-biologically enhanced form (i.e., a conductive polymer bound to magnetic nanoparticles) so that a user can functionalize the composition 212 with any desired binding pair member to customize the composition 212 to any desired target analyte. In another embodiment, the composition 212 is a BEAM nanoparticle composition with a binding pair member complementary to a target analyte. In this embodiment, the kit is prepared specifically for a particular target analyte. The kit 200 also can include a reaction vessel 220 (i.e., a container for mixing the composition 212 and a sample to be analyzed), a container 230 containing a detection label complementary to the target analyte or to the binding pair member, and/or a lateral flow assay device 240 having a capture region 242 (i.e., which can include an immobilized binding pair member complementary to the target analyte). The kit 200 can generally include a variety of other optional components (not shown) that may be desired and/or appropriate, for example a magnet, wash reagents, detector reagents (i.e., which cause the detection label to provide its detectable signal), positive and/or negative control reagents, assay kit instructions, and other additives (e.g., stabilizers, buffers). The relative amounts of the various reagents may be varied widely, to provide for concentrations in solution of the reagents that substantially optimize the sensitivity of the assay. Particularly, the reagents may be provided as dry powders (e.g., lyophilized) which on dissolution will provide for a reagent solution having the appropriate concentrations for combining with the sample.

EXAMPLES

The following Examples illustrate the disclosed compositions and methods, but are not intended to limit the scope of any claims thereto.

Aniline, N,N-dimethylformamide (DMF), Tween-20, tris buffer, phosphate buffer, and phosphate-buffered saline (PBS) were purchased from Sigma-Aldrich (St. Louis, Mo.). Antibodies (Rabbit anti-*E. coli* O157:H7) were obtained from Biodesign (ME). Other reagents used were analytical grade. All chemicals and diluents were prepared with doubly deionized water with conductivity below 0.1 µS/cm.

Example 1

Synthesis of a Conductive Polyaniline—Iron Oxide Particulate Composition

Synthesis of EAM Nanoparticles.

A particulate composition according to the disclosure was synthesized by the oxidative polymerization of aniline monomer (FW: 91.13) made electrically active by acid doping (i.e., the addition of small quantities of foreign atoms, particularly protonating acids such as hydrochloric acid and sulfuric acid, that can release protons) in presence of gamma iron (III) oxide nanoparticles ($\gamma$-$Fe_2O_3$, FW: 159.69; available from Sigma-Aldrich (St. Louis, Mo.)). The $\gamma$-$Fe_2O_3$ nanoparticles were first dispersed in a mixture of 50 ml 1M HCl, 10 ml de-ionized water and 0.4 ml of aniline. The mixture was sonicated for 1 h in an ice bath in order to disintegrate the agglomerated nanoparticles. This was followed by a slow, drop-wise addition of an oxidant (ammonium persulfate) to the mixture with continuous stirring. The ice bath reaction was continued for an additional 4 h. The aniline polymerized and formed polyaniline bound to the iron oxide nanoparticles, as evidenced by a color change. The final electrically active magnetic ("EAM") nanoparticle product obtained was filtered, followed by repeated washings with 1M HCl, methanol, and diethyl ether, and then dried at room temperature for 48 h to obtain a dark green powder. Four different weight ratios of $\gamma$-$Fe_2O_3$ to aniline monomer (1:0.1, 1:0.4, 1:0.6, and 1:0.8) were synthesized using the above procedure.

Structural Characterization.

The structural morphology of the EAM nanoparticles was studied using both Transmission Electron Microscopy (JEOL 100CX II) and Scanning Electron Microscopy (JEOL 6400V) (Japan Electron Optics Laboratories). The shapes and sizes of the nanoparticles were estimated using the electron microscopic images. Crystalline or amorphous nature of the nanoparticles was also studied by Selected Area Electron Diffraction using the JEOL 2200FS 200 kV field emission TEM. X-Ray Energy Dispersive Spectroscopy was also carried out for the EAM nanoparticles using the JEOL 2200FS TEM for determining the percentage composition of the polymer and the gamma iron-oxide nanoparticles in the synthesized nanopolymers. FIGS. 3A to 3D show TEM images of EAM nanoparticles at different weight ratios of $\gamma\text{-}Fe_2O_3$ to aniline (A: 1:0.1, B: 1:0.4, C: 1:0.6, and D: 1:0.8). From the figures, the resulting EAM nanoparticles have a particle size generally depending on the weight ratio of magnetic nanoparticles: monomer, for example ranging from about 10 nm (at a ratio of 1:0.1) to about 200 nm (at a ratio of about 1:0.8).

Magnetism Measurement.

Figure 4:
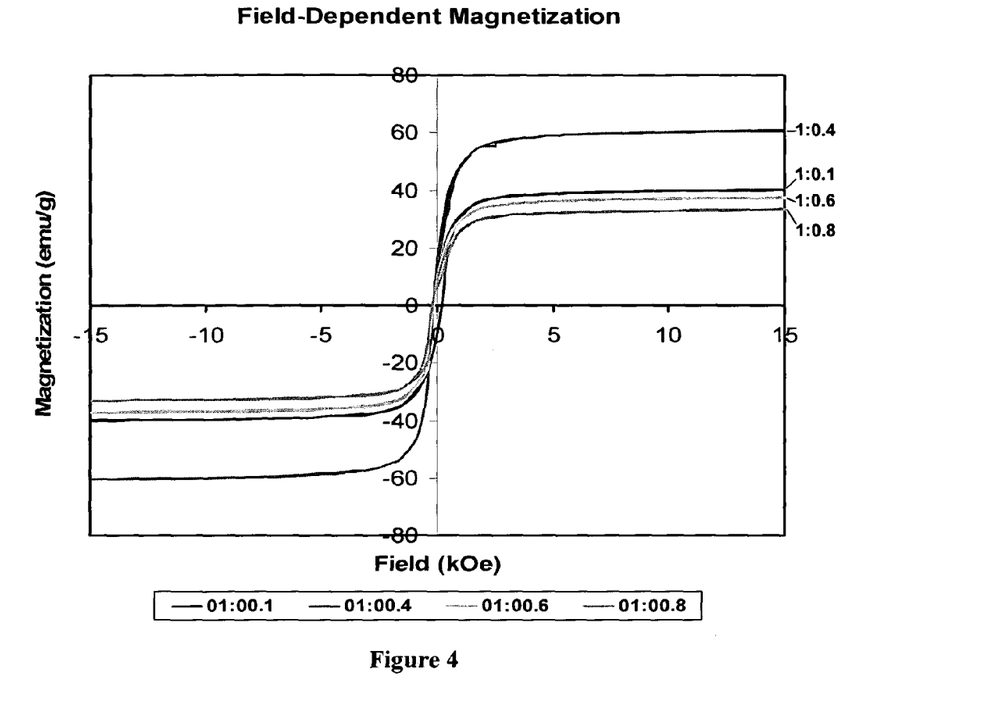
FIG. 4 is a graph showing field-dependent magnetization hysteresis measurements of the different conductive polyaniline-$\gamma$-Fe$_2$O$_3$ complexes of FIGS. 3A to 3D.

A Quantum Design MPMS SQUID (Superconducting quantum information device) magnetometer was used for magnetic characterization and room temperature hysteresis measurements of the synthesized EAM nanoparticles. For the hysteresis loop measurement, the magnetic samples were subjected to a magnetic field cycling between +20 kOe and −20 kOe, while the temperature was maintained constant at 300K. The saturation magnetization values of each sample was determined in emu/gm and compared with that of pure gamma iron-oxide particles. For each of the four weight ratios synthesized, the saturation magnetization was between 33.5 emu/g and 61.1 emu/g, as illustrated in FIG. 4. The coercivity and retentivity of the magnetic nanoparticles were also studied form the room temperature hysteresis measurements in order to study the presence of super paramagnetic behavior in these samples. The synthesized EAM nanoparticles showed low values of coercivity and retentivity.

Electrical Conductivity Measurements.

The electrical conductivity of the synthesized magnetic nanoparticles was evaluated in both liquid and solid forms. For conductivity measurements in liquid form, the magnetic nanoparticles were dissolved in appropriate solvents and the conductivity was measured with the help of a conductivity meter (ACORN TDS 5 Meter). Solid conductivity was measured with the help of a Four Point Probe (Lucas/Signatone Corporation, Pro4; CA, USA).

Example 2

Synthesis of *E. coli*-Specific BEAM Nanoparticles

Synthesis of EAM Nanoparticles.

5 ml of 0.4 M of iron (III) oxide nanopowder ($Fe_2O_3$) and an aniline solution (0.188 ml aniline in 5 ml distilled water) were mixed with 40 ml of 0.2 mM ammonium persulfate (APS), and diluted into 80 ml of 1 M hydrochloric acid, and then reacted for 30 min. The mixture was then washed with 5% ammonia hydroxide to rinse out excess hydrochloric acid. The resulting EAM nanoparticle product was filtered with filter paper, dissolved in 5 ml dimethylformamide (DMF), and any undissolved product was eliminated by filtration. The soluble polymer was precipitated by adding 2 ml of 2 M HCl in DMF. After filtration, any residual solvent was evaporated, and the final protonated EAM nanoparticle product was dissolved in phosphate buffer saline (PBS) containing 10% (v/v) DMF.

Antibody Binding to Conductive Polymer.

Rabbit anti-*E. coli* O157:H7 antibody was used as supplied. The antibody was conjugated to the EAM nanoparticles by (1) adding 800 µl of 150 µg/ml antibody to 8 ml of 0.1 g/ml of the EAM nanoparticles and then (2) allowing the mixture to react for 30 min. Then, 1 ml of 0.1 M Tris 0.5% casein was added and left to react again for 30 min. The mixture was centrifuged at 13000 rpm for 3 min. The addition of the 0.1 M Tris 0.5% casein and centrifugation was repeated three times, thereby forming the BEAM nanoparticles. The BEAM nanoparticles were then added to 0.1 M LiCl and stored in the refrigerator when not in use.

Example 3

Synthesis of *B. anthracis*-Specific BEAM Nanoparticles

Synthesis of BEAM Nanoparticles.

EAM nanoparticles from Example 1 were conjugated with mouse monoclonal antibodies to *B. anthracis* spores (clone 2C3) The EAM nanoparticles and the target-specific antibodies were combined and incubated in a sodium-phosphate buffer to directly bind the antibodies to the conductive polyaniline, thereby forming the BEAM nanoparticles. The concentrations of the antibodies and the EAM nanoparticles in the buffer were maintained at 150 µg/ml and 100 mg/ml, respectively. Centrifugation and reconstitution was used to remove unconjugated antibodies.

*Bacillus* Sample Preparation.

Figure 5:
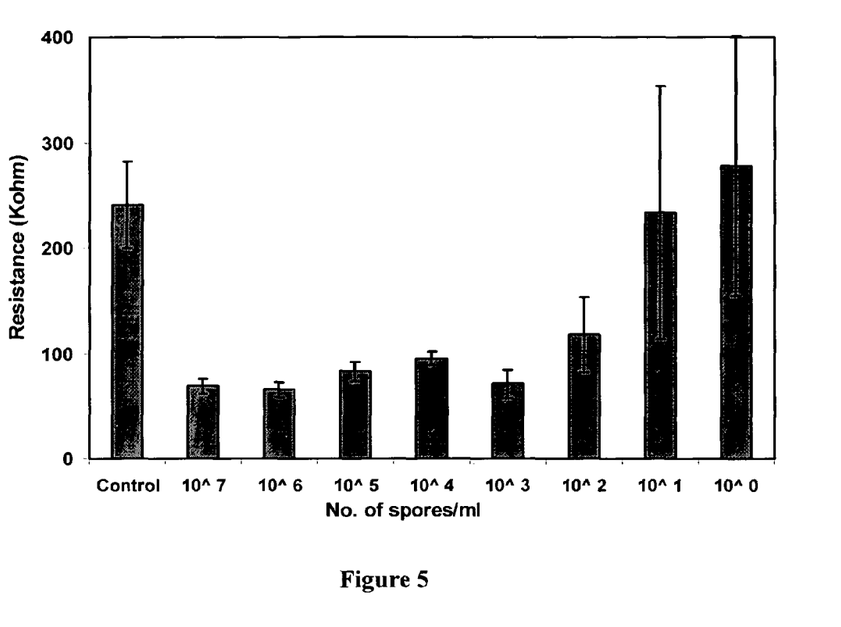
FIG. 5 is a bar graph illustrating the sensitivity of a *Bacillus anthracis* assay using BEAM nanoparticles.

Seven serial dilutions were performed beginning with a pure culture of the target antigen. A solution in 0.1% peptone water was formed containing 20% of BEAM nanoparticles (200 mg) and 10% *B. anthracis* antigen of a specified dilution. After a brief incubation period (10 min), an antigen-BEAM nanoparticle complex formed in the solution. The solution was exposed to a magnetic field which held the complexed antigen-BEAM nanoparticles in place while supernatant was removed, eliminating any unbound antigens. The particles were reconstituted and resuspended as a sample concentrate in 0.1% peptone water and applied to a conductimetric biosensor for testing (i.e., a lateral flow conductimetric capture assay device as described in the copending Alocilja application). The biosensor was able to detect *Bacillus anthracis* spores at a concentration as low as about $10^2$ spores/ml as shown in FIG. 5. The specificity study of the biosensor was performed in pure cultures of *E. coli* CN13 and was found to be specific for *Bacillus anthracis* spores.

Example 4

Synthesis of DNA-Specific BEAM Nanoparticles

The conductive polyaniline nanoparticles of Example 1 were immersed in 22.5 µM of a phosphorylated specific oligonucleotide probe of *B. anthracis* pag A gene (5'-PO4-GGAAGAGTGAGGGTGGATACAGGCTC-GAACTGGAGTGAAGTGTTACCGCA-3') (SEQ ID NO: 1) containing 0.1 M 1-ethyl-3-(3-dimethylaminopropyl-1)-carbodiimide (EDAC) and 10 mM acetate buffer (pH: 5.2) for 10 h with gentle stirring in an incubator shaker at room temperature. The ssDNA-bound nanoparticles were then separated by a magnetic separator (Spherotech, Ill.) and washed with a 0.1% SDS phosphate buffer (pH: 7.3) for 5 minutes to remove any unbound DNA probes. Finally, the ssDNA-bound nanoparticles were suspended in PBS (pH-7.4) and stored at 4° C.

The disclosure particularly relates EAM and BEAM nanoparticles useful in assays and detection devices for rapid pathogen detection. The disclosure provides a new class of compositions particularly for the detection of pathogens such as *Escherichia coli* O157:H7, *Bacillus anthracis*, and *Bacillus cereus*. A conductimetric biosensor device using antibody-bound BEAM nanoparticles can provide antibody-antigen binding and has the sensitivity to detect as low as about $10^0$ to about $10^1$ cfu/mL of *E. coli* or *B. anthracis* in 2 to 10 minutes. The BEAM nanoparticles can thus detect other disease-causing bacteria, toxins, pathogens, chemicals and potential biowarfare agents such as *Salmonella* and *Listeria monocytogenes*. Thus, the compositions of the disclosure can be particularly used to detect pathogens, proteins, and other biological materials of interest in food, water, and environmental samples. The BEAM nanoparticles can also be used for onsite diagnostics and against potential bioterrorism. Users include food processing plants, meat packing facilities, fruit and vegetable packers, restaurants, food and water safety inspectors, food wholesalers and retailers, farms, homes, medical profession, import border crossing, the police force, military, space habitation, and national security.

Because other modifications and changes varied to fit particular operating requirements and environments will be apparent to those skilled in the art, the disclosure is not considered limited to the example chosen for purposes of illustration, and covers all changes and modifications which do not constitute departures from the true spirit and scope of this disclosure.

Accordingly, the foregoing description is given for clearness of understanding only, and no unnecessary limitations should be understood therefrom, as modifications within the scope of the disclosure may be apparent to those having ordinary skill in the art.

Throughout the specification, where the compositions, processes, or apparatus are described as including components, steps, or materials, it is contemplated that the compositions, processes, or apparatus can also comprise, consist essentially of, or consist of, any combination of the recited components or materials, unless described otherwise. Combinations of components are contemplated to include homogeneous and/or heterogeneous mixtures, as would be understood by a person of ordinary skill in the art in view of the foregoing disclosure.

What is claimed is:

1. A method of detecting the presence of a target analyte in a sample, the method comprising:

(a) providing a biologically enhanced, electrically active magnetic (BEAM) nanoparticle composition comprising (i) a particulate composition comprising: a conductive polymer bound to magnetic nanoparticles, and (ii) a binding pair member bound to the conductive polymer of the particulate composition, wherein the binding pair member is complementary to the target analyte, the particulate composition ranges in size from about 1 nm to about 500 nm, and the weight ratio of conductive polymer to magnetic nanoparticles in the particulate composition ranges from about 0.1 to about 1;

(b) contacting the BEAM nanoparticle composition with the sample for a time sufficient to bind any target analyte in the sample to the binding pair member of the BEAM nanoparticles, thereby forming an analyte-nanoparticle complex;

(c) applying a magnetic field to the sample and removing a portion of the sample that is substantially free from the analyte-nanoparticle complex, thereby forming a sample concentrate that contains substantially all of the analyte-nanoparticle complex; and, (d) determining the presence of the target analyte in the sample by detecting the analyte-nanoparticle complex in the sample concentrate.

2. The method of claim 1, wherein detecting the analyte-nanoparticle complex in step (d) further comprises:

(d1) contacting the sample concentrate with a detection label for a time sufficient to bind the detection label to the analyte-nanoparticle complex, thereby forming a label-analyte-nanoparticle complex, wherein either (i) the detection label is complementary to the target analyte and the detection label binds to the target analyte bound to the analyte-nanoparticle complex or (ii) the detection label is complementary to the binding pair member and the detection label binds to a free binding pair member of the analyte-nanoparticle complex;

(d2) removing free detection label that is not bound in the label-analyte-nanoparticle complex from the sample concentrate; and, (d3) detecting the detection label remaining in the sample concentrate that is bound in the label-analyte-nanoparticle complex.

3. The method of claim 2, wherein the detection label comprises a label selected from the group consisting of enzymes, chromogenic substrates, chromophores, radioisotopes, fluorescent molecules, chemiluminescent molecules, phosphorescent molecules, direct visual labels, and combinations thereof.

SEQUENCE LISTING

<160> NUMBER OF SEQ ID NOS: 1

<210> SEQ ID NO 1
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 1
ggaagagtga gggtggatac aggctcgaac tggagtgaag tgttaccgca        50

4. The method of claim 1, wherein:
(i) the magnetic nanoparticles comprise ferromagnetic nanoparticles;
(ii) the conductive polymer is selected from the group consisting of polyanilines, polyparaphenylenes, polyparaphenylene vinylenes, polythiophenes, polypyrroles, polyfurans, polyselenophenes, polyisothianapthenes, polyphenylene sulfides, polyacetylenes, polypyridyl vinylenes, conductive carbohydrates, conductive polysaccharides, derivatives thereof, combinations thereof, blends thereof with other polymers, and copolymers of the monomers thereof; and
(iii) the binding pair member is selected from the group consisting of antibodies, antibody fragments, antigens, biotin, avidin and derivatives thereof, hormones, hormone receptors, polynucleotides, aptamers, whole cells, and combinations thereof.

5. The method of claim 1, wherein:
(i) the magnetic nanoparticles comprise at least one of Fe(II) and Fe(III);
(ii) the conductive polymer is selected from the group consisting of polyanilines, polypyrroles, polythiophenes, derivatives thereof, combinations thereof, blends thereof with other polymers, and copolymers of the monomers thereof; and
(iii) the binding pair member is selected from the group consisting of antibodies, antibody fragments, antigens, biotin, avidin and derivatives thereof, hormones, hormone receptors, polynucleotides, aptamers, whole cells, and combinations thereof.

6. The method of claim 1, wherein:
(i) the magnetic nanoparticles comprise $\gamma$-$Fe_2O_3$ (maghemite);
(ii) the conductive polymer comprises polyaniline; and
(iii) the binding pair member comprises an antibody.

7. The method of claim 1, wherein the particulate composition comprises particles ranging in size from about 10 nm to about 200 nm.

8. The method of claim 1, wherein the weight ratio of conductive polymer to magnetic nanoparticles in the particulate composition ranges from about 0.4 to about 0.8.

9. The method of claim 1, wherein the binding pair member is selected from the group consisting of an anti-*Escherichia coli* $O_{157}$:H7 antibody, an anti-*Bacillus anthracis* antibody, and an anti-*Bacillus cereus* antibody.

10. The method of claim 1, wherein the particulate composition further comprises a label bound to the conductive polymer.

11. The method of claim 10, wherein the label is selected from the group consisting of enzymes, chromogenic substrates, chromophores, radioisotopes, fluorescent molecules, chemiluminescent molecules, phosphorescent molecules, direct visual labels, and combinations thereof.

12. The method of claim 1, wherein detecting the analyte-nanoparticle complex in step (d) further comprises:
(d1) removing BEAM nanoparticles that are not bound to an analyte from the sample concentrate; and
(d2) conductimetrically detecting the analyte-nanoparticle complex in the sample concentrate.

13. The method of claim 12, wherein the particulate composition is in the form of a composite with the conductive polymer coating the magnetic nanoparticles and providing a substrate for attachment of the binding pair member bound to the conductive polymer.

14. The method of claim 1, wherein the weight ratio of conductive polymer to magnetic nanoparticles in the particulate composition ranges from 0.1 to 0.8.

15. The method of claim 1, wherein the weight ratio of conductive polymer to magnetic nanoparticles in the particulate composition ranges from 0.1 to 0.6.

16. The method of claim 1, wherein the weight ratio of conductive polymer to magnetic nanoparticles in the particulate composition ranges from 0.6 to 1.

17. The method of claim 1, wherein the particulate composition ranges in size from 50 nm to 100 nm.

18. The method of claim 1, wherein the particulate composition ranges in size from 10 nm to 90 nm.

19. The method of claim 1, wherein the particulate composition is in the form of a composite with the conductive polymer coating the magnetic nanoparticles and providing a substrate for attachment of the binding pair member bound to the conductive polymer.

* * * * *